US010441333B2

(12) United States Patent
Zeitani

(10) Patent No.: US 10,441,333 B2
(45) Date of Patent: Oct. 15, 2019

(54) METHOD OF REINFORCING A STERNUM AFTER A STERNOTOMY OR A STERNAL FRACTURE

(71) Applicant: SIC BREVETTI S.R.L., Rome (IT)

(72) Inventor: Jacob Zeitani, Rome (IT)

( * ) Notice: Subject to any disclaimer, the term of this patent is extended or adjusted under 35 U.S.C. 154(b) by 100 days.

(21) Appl. No.: 14/011,533

(22) Filed: Aug. 27, 2013

(65) Prior Publication Data

US 2015/0066029 A1    Mar. 5, 2015

Related U.S. Application Data

(63) Continuation of application No. 10/597,659, filed as application No. PCT/IT2005/000076 on Feb. 15, 2005, now Pat. No. 8,523,860.

(30) Foreign Application Priority Data

Feb. 16, 2004  (IT) .............................. RM2004A0082

(51) Int. Cl.
*A61B 17/80*    (2006.01)
*A61B 17/82*    (2006.01)

(52) U.S. Cl.
CPC ........ *A61B 17/823* (2013.01); *A61B 17/8076* (2013.01)

(58) Field of Classification Search
CPC .................... A61B 17/823; A61B 17/8076
USPC ............................................ 606/74–75, 905
See application file for complete search history.

(56) References Cited

U.S. PATENT DOCUMENTS

| | | |
|---|---|---|
| 1,157,202 A | 10/1915 | Bates |
| 2,486,303 A | 4/1948 | Longfellow |
| 3,384,078 A | 5/1968 | Gauthier |
| 3,509,873 A | 5/1970 | Karlin |
| 3,522,799 A | 8/1970 | Gauthier |

(Continued)

FOREIGN PATENT DOCUMENTS

| | | |
|---|---|---|
| CN | 1917823 | 2/2007 |
| EP | 1732460 | 5/2010 |

(Continued)

OTHER PUBLICATIONS

Restriction Requirement issued in U.S. Appl. No. 10/597,659 dated Aug. 3, 2009.

(Continued)

*Primary Examiner* — Jan Christopher L Merene

(57) ABSTRACT

A method for reinforcing a sternum after a sternotomy or a sternal fracture. The method includes i) applying a plurality of elongated members along at least one longitudinal lateral edge of the sternum, wherein the elongated members are each provided with a first connection part and a second connection part; ii) slidably joining a first connection part of a first elongated member with a second connection part of an adjacent preceding elongated member along the longitudinal lateral edge of the sternum; iii) slidably joining a second connection part of the first elongated member with a first connection part of an adjacent following elongated member along the same longitudinal lateral edge of the sternum; iv) fitting a projecting portion of one or more of said elongated members in an intercostal space adjacent to the longitudinal lateral edge of the sternum; and v) fixing the elongated members to the sternum.

22 Claims, 5 Drawing Sheets

(56) References Cited

U.S. PATENT DOCUMENTS

| | | |
|---|---|---|
| 4,583,541 A | 4/1986 | Barry |
| 5,607,425 A | 3/1997 | Rogozinski |
| 5,616,142 A | 4/1997 | Yuan |
| 5,620,444 A | 4/1997 | Assaker |
| 5,704,936 A | 1/1998 | Mazel |
| 5,779,629 A | 7/1998 | Hohlen |
| 5,989,250 A | 11/1999 | Wagner |
| 6,139,493 A | 10/2000 | Koros |
| 6,241,730 B1 | 6/2001 | Alby |
| 6,296,644 B1 | 10/2001 | Saurat |
| 6,511,423 B2 | 1/2003 | Farley |
| 6,540,769 B1 | 4/2003 | Miller, III |
| 6,712,821 B2 | 3/2004 | Gabbay |
| 7,033,377 B2 | 4/2006 | Miller, III |
| 7,083,621 B2 | 8/2006 | Shaolian |
| 7,186,254 B2 | 3/2007 | Dinh |
| 7,318,825 B2 | 1/2008 | Butler |
| 7,491,168 B2 | 2/2009 | Raymond |
| 7,588,589 B2 | 9/2009 | Falahee |
| 8,523,860 B2 * | 9/2013 | Zeitani ............... 606/71 |
| 8,992,530 B2 * | 3/2015 | Madjarov ............ 606/74 |
| 2002/0095071 A1 | 7/2002 | Farley |
| 2002/0111538 A1 | 8/2002 | Wright |
| 2002/0138077 A1 | 9/2002 | Ferree |
| 2003/0083694 A1 | 5/2003 | Miller, III |
| 2003/0212399 A1 | 11/2003 | Dinh |
| 2004/0010256 A1 * | 1/2004 | Gabbay ............... 606/71 |
| 2004/0092929 A1 | 5/2004 | Zindrick |
| 2004/0258732 A1 * | 12/2004 | Shikinami ........... 424/426 |
| 2005/0043732 A1 | 2/2005 | Dalton |
| 2005/0137597 A1 | 6/2005 | Butler |
| 2005/0159651 A1 | 7/2005 | Raymond |
| 2005/0277939 A1 | 12/2005 | Miller, III |
| 2007/0043371 A1 | 2/2007 | Teague |
| 2008/0221578 A1 | 9/2008 | Zeitani |

FOREIGN PATENT DOCUMENTS

| | | |
|---|---|---|
| RU | 2 199 288 | 2/2003 |
| RU | 2371138 | 10/2009 |
| WO | 9320771 | 10/1993 |
| WO | 02/067795 | 9/2002 |

OTHER PUBLICATIONS

Reply to Restriction Requirement issued in U.S. Appl. No. 10/597,659 dated Aug. 3, 2009.
Non-Final Office Action issued in U.S. Appl. No. 10/597,659 dated Dec. 24, 2009.
Reply to Non-Final Office Action issued in U.S. Appl. No. 10/597,659 dated Dec. 24, 2009.
Final Office Action issued in U.S. Appl. No. 10/597,659 dated Sep. 3, 2010.
Reply to Final Office Action issued in U.S. Appl. No. 10/597,659 dated Sep. 3, 2010.
Non-Final Office Action issued in U.S. Appl. No. 10/597,659 dated Feb. 6, 2013.
Reply to Non-Final Office Action issued in U.S. Appl. No. 10/597,659 dated Feb. 6, 2013.
Notice of Allowance issued in U.S. Appl. No. 10/597,659 dated May 20, 2013.

* cited by examiner

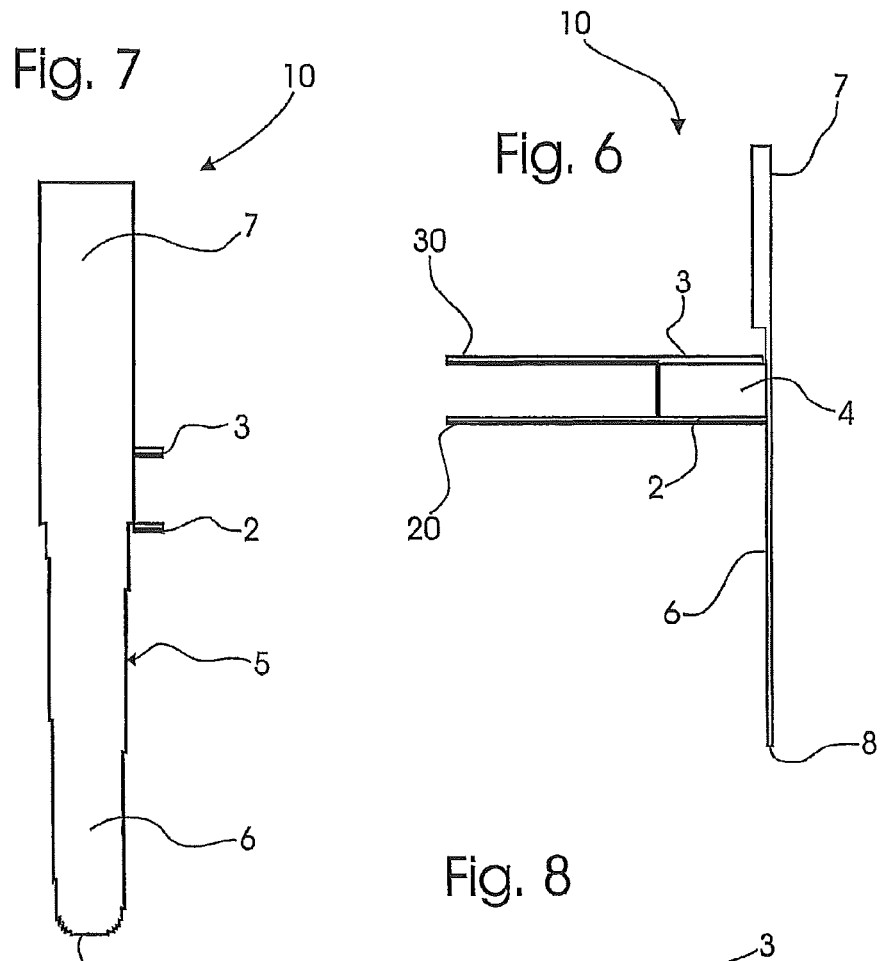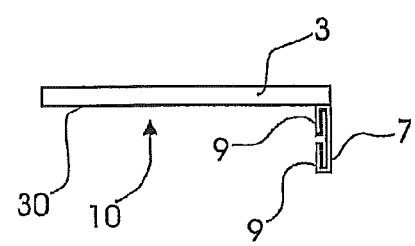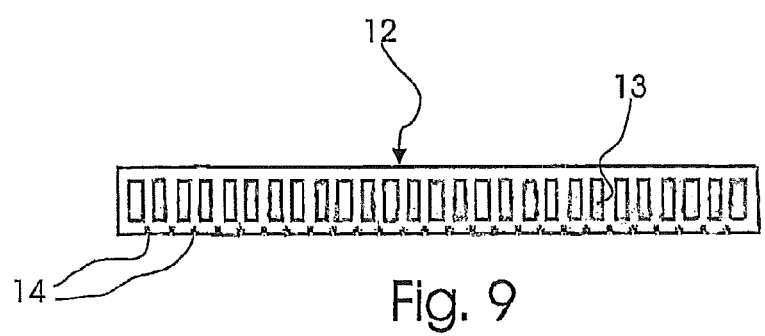

METHOD OF REINFORCING A STERNUM AFTER A STERNOTOMY OR A STERNAL FRACTURE

CROSS-REFERENCE TO RELATED APPLICATIONS

This application is a continuation application claiming the benefit of the U.S. patent application Ser. No. 10/597,659 projected to issue as the U.S. Pat. No. 8,523,860 on Sep. 3, 2013, which U.S. patent application Ser. No. 10/597,659 is a national phase entry based on the PCT application PCT/IT2005/000076 that claims the Paris Convention priority of the Italian patent application RM2004A000082 with a filing date of Feb. 16, 2004.

TECHNICAL FIELD OF THE INVENTION

This invention relates to a method of reinforcing a sternum after a sternotomy or a sternal fracture.

BACKGROUND OF THE INVENTION

The median sternotomy is a very usual operation in the field of heart surgery.

The sternum or its portion of a patient is sawn by a saw or other cutting means. When all the sternum is severed in two, its sternal halves are spread apart laterally the one from the other so that mediastinum structures can be exposed. As a result, a large aperture is formed in the thoracic cavity, which permits an optimal surgical access to the heart and great vessels and also is well tolerated by the patient.

Once the operation is completed, the two sternal halves are rejoined. Traditionally, several means, such as Mersilene fibres, steel wires, metal and plastic bands, nitinol clamps, etc. are used for a sternal closure in order to assure the sternal stability and the recovery of the patient. The most usual current method of doing this is to use steel wires around the sternum passing through intercostal spaces.

However, both the medial sternotomy and the current methods are not free of complications. The complications of the sternal wound, usually due to the sternum instability, range from prolonged thoracic pains, which cause inconveniences and related respiratory disorders up to the dehiscence of the wound at the risk of infections and mediastinitis.

U.S. Pat. No. 4,583,541 already provides a sternal stabilizer for holding a severed sternum closed. Such a stabilizer consists essentially of a single strap-like member, which is adapted to overlie, in longitudinal and centrally relation, the anterior surface of a divided sternum of a patient. Such a strap-like member is provided with a plurality of pairs of through holes. A plurality of wires extend from the sternum posterior surface through holes formed in the sternum concentrically to the strap-like member through holes and are tied or twisted together within a central groove.

The above patent would intend to overcome problems occurring with the complications seen after median sternotomies. These problems range from wires breaking, wires protruding through the skin e.g. upon a patient's slimming, separation of the sternal halves, failure of the sternum to heal, infections and loose or unstable sternal halves.

Differently from the above patent that intends to protect a sternal stabilizer which appears to be limited in its function due to the need of fitting together holes in the sternum and those in the strap-like member, this invention aims to create a partial or full reinforcement for one sternal half or both, considering that sternotomy operations are carried out more often in elderly patients, whose skeletal system is losing more and more its strength in time.

Therefore, an object of the present invention is to provide a device adapt to be used in the sternal closure that provides a lateral reinforcement to the sternal halves as well as to both anterior and posterior portions of the sternum.

Another object of the invention is to perform a sternal closure similar to that could be made through a wire binding, without any risk of rubbing of the wire on the sternum which could generate subsequent lesions and consequent partial or complete fractures and wire loosening.

A further object of the invention is to permit a closure also in parts affected by partial or complete fractures of the sternum, which are subsequent to a primary operation.

Yet a further object of the invention is to allow the sternal halves be closed during an operation for sternal dehiscence particularly without being necessary to separate any adherence being formed in meanwhile, which would involve a high risk of damage to the heart and any bypasses and relevant ducts.

Yet another object of the invention is to reinforce sternums which can be closed again by traditional methods at the risk of complications, owing to ageing or degeneration processes, such as the osteoporosis process, on patients that are affected also by diabetes, respiratory insufficiency, or obesity, or that have been subjected to paramedian sternotomies.

SUMMARY OF THE INVENTION

Therefore, the invention provides a sternum reinforcing method and device to be used after a sternotomy or a sternal fracture, wherein the device comprises at least an elongated modular member, which is designed to be located on a surface portion of an anterior edge of a sternum and provided with a first and a second connection parts, said first part of said elongated modular member being adapted to join with a second connection part of a preceding elongated modular member, said second part of said elongated modular member being adapted to join with a first part of a following elongated modular member; each elongated modular member being further provided with a projecting portion designed to be fitted in an intercostal space adjacent to the lateral edge of the sternum.

BRIEF DESCRIPTION OF THE DRAWINGS

The present invention will be described referring to two preferred embodiment thereof, with connection to the enclosed drawing, in which:

FIG. 6 shows an elevation side view of the sternum reinforcing device in FIG. 5, being rotated 90 degrees in the drawing sheet;

FIG. 7 shows a top plan view of the sternum reinforcing device in FIG. 6;

FIG. 8 shows an end plan view of the sternum reinforcing device in FIG. 6;

FIG. 9 shows a plan view of a retaining splint according to the present invention;

DETAILED DESCRIPTION OF THE DRAWINGS

Figure 1:
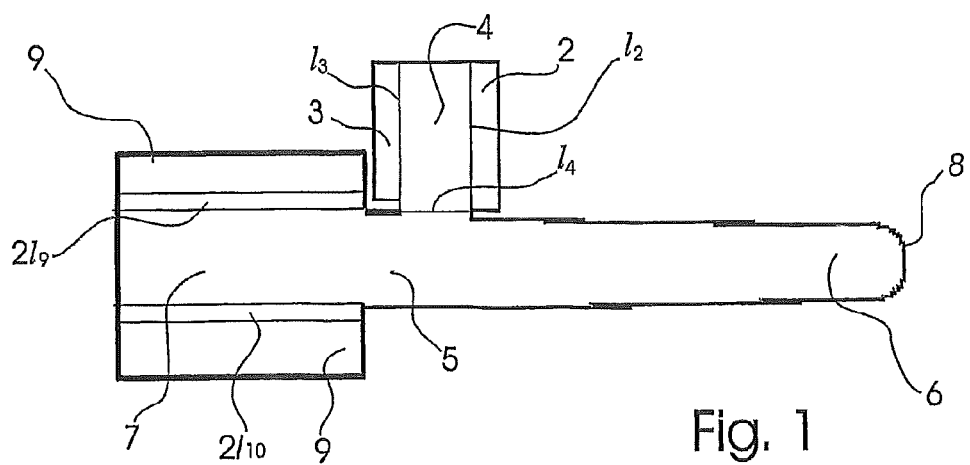
FIG. 1 shows a plan view of a plate blank which is shaped to obtain a first embodiment of the sternum reinforcing device according to the present invention.

With reference to the drawings, shown in the plan view of FIG. 1 is a first embodiment of the device according to the present invention in a semifinished condition, i. e. in the form of a punched plate blank (totally lying in the plane of the drawing sheet).

The reinforcing device can be manufactured from a sheet of biocompatible material, e. g. stainless steel, being shaped by punching or other cutting process such as electrical discharge machining or laser cutting, etc. into a modular elongated member.

Mechanical and technological characteristics of the material are selected in order to assure suitable mechanical working properties, usefulness and functionality to the device. Obviously, the reinforcing device can be obtained by machining as well as by casting, or from a not metallic material and by a different working method.

The elongated modular member 1 is shaped in a such way that a small body portion 4 is made in the form of a gusset in a intermediate position of the elongated modular member 1. The body portion 4 is contiguous to a central portion 5 of the modular member 1, a bending line $I_4$ being provided between them. Formed laterally to the body portion 4 are edges 2, 3 bordering on the body portion 4 along respective folding lines $I_2$, $I_3$, but being separated from the central portion 5.

The modular member 1 has connection parts in the form of arms 6, 7 being extended the one in one direction, the other in the opposite direction, with respect to the central portion 5. The arm 6, having a flat rectangular cross-sectioned profile, is slightly tapered toward its free end 8. The arm 7 is extended transversally by fins 9, 9, which can doubly bent by virtue of pairs of parallel bending lines $2I_9$, $2I_{10}$.

Figure 2:
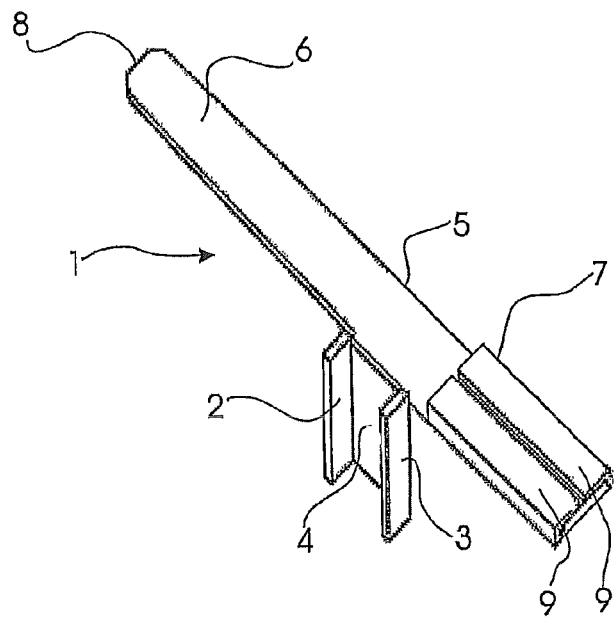
FIG. 2 shows in a perspective view the sternum reinforcing device in the form of an elongated member obtained by the plate blank in FIG. 1.

The punched plate blank in FIG. 1 is shown erected, ready to be used, in the perspective view in FIG. 2. In this figure the body portion 4 is shown is orthogonally bent downward, thus as if it penetrates the drawing sheet, and the side parallel edges 2 and 3 of the body portion 4 are bent substantially at right angle outwards to form an U-shaped cross-section adapted to retain clamping means (to be described below).

Figure 3:
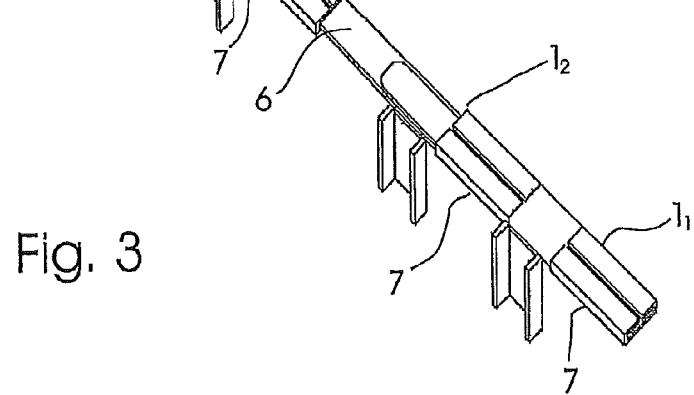
FIG. 3 shows in a perspective view a sternum reinforcing device having three elongated members as that one in FIG. 2, which are mutually engaged consecutively.

Fins 9, 9 are doubly bent to form a so called channel hollow profile cross-section. Fins 9, 9 are bent upwards (as shown in FIGS. 2 and 3) or downwards (as later shown in FIGS. 5, 6, 7, 8, 10, and 11) with respect to the drawing sheet and then in parallel to the latter, by virtue of pairs of parallel bending lines $2I_9$, $2I_{10}$. It should be evident that the choice of bending the fins 9, 9 upwards or downwards in order to create a hollow cross-section, can be suggested by a more comfortable use in installing the device in the first case, and by a more finished front surface of the same device once it is in situ, in the second case, and by other remarks easy to understand.

In FIG. 3 there is shown the sternum reinforcing device of the invention as a unit of three elongated modular members according to the first embodiment in their assembling step. Thus, this unit will be installed as shown in a diagrammatic perspective view in FIG. 11. The elongated modular members are indicated generally as 1 and distinguished by an index in a plurality $1_1$, $1_2$, ..., $1_n$, n being generally equal to 4 at the most.

As seen in FIG. 3, the elongated modular members $1_1$, $1_2$, $1_3$ are connected consecutively by means of prismatic sliding couplings, whereby the male arm 6 of the modular member $1_1$ is fitted in the female arm 7 of the consecutive modular member $1_2$, and the male arm 6 of the latter is fitted in the female arm of the consecutive modular member $1_3$. The elongated modular members $1_1$ and $1_2$ fully interpenetrate, the end of the female part of the one abutting on the projecting edge 2 of the other. The member $1_3$ is shown as spaced from the others.

The sizes of the body portion 4 are such that it can be fitted in the intercostal space of any patient. On the other hand, the longitudinal sizes of the arms 6, 7 and the amount of their mutual sliding are selected in such a way to allow the one elongated member and the consecutive one to be spaced so that they are adjusted to any rib width of a patient. In other words, a modular member can be spaced from the consecutive one in the measure required for fitting the body portion in the relevant intercostal space, without loosing their mutual contact.

Figure 4:
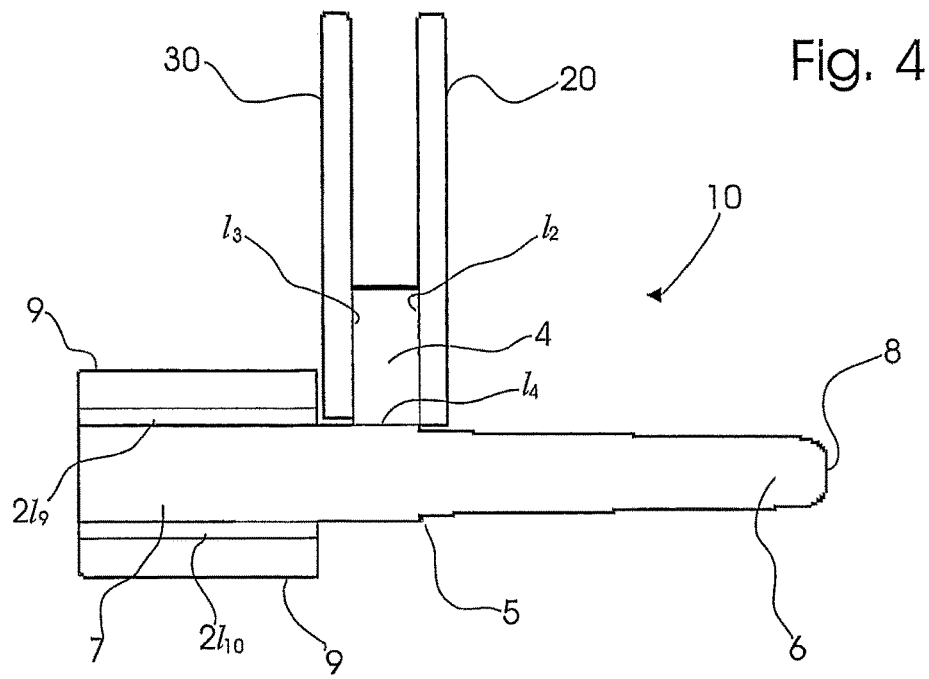
FIG. 4 shows a plan view of a plate blank which is shaped to obtain a second embodiment of the sternum reinforcing device according to the present invention.

With reference to FIG. 4, therein a second embodiment of the modular device according to the present invention, indicated as 10 as a whole, is shown by a plan view similar to that in FIG. 1.

For clarity sake, in describing the second embodiment similar reference numerals and signs are used to indicate parts that are identical or similar to those of the first embodiment. The second embodiment differs from the first embodiment as the edges 2, 3 extend from the body portion 4 to form legs 20, 30.

Figure 5:
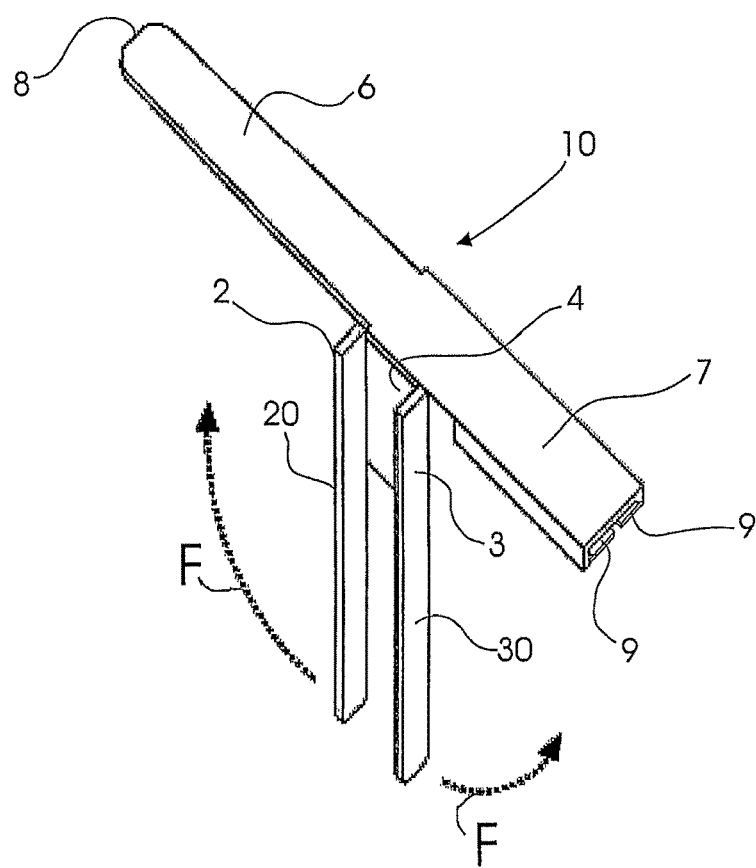
FIG. 5 shows in a perspective view the sternum reinforcing device in the form of an elongated member obtained by the plate blank in FIG. 4.

The punched plate blank in FIG. 4 is shown in its erected form, ready for its use, in the perspective view of FIG. 5. Therein the body portion 4 is shown bent orthogonally downwards, thus as if it penetrates the drawing sheet, and the two lateral legs 20 and 30 are bent substantially 90 degrees outwards. As for the first embodiment, the fins 9, 9 are bent to form a channel-shaped cross-section. The counter-rotating arrows F indicate that the lateral legs 20, 30 can be bent in the opposite direction to abut themselves on the internal surface of the thorax in correspondence with the respective ribs in order to create a suitable clamping. Therefore, a material of which the reinforcing device is made has to be suitably bendable also only by hand.

The second embodiment of the invention is shown by three orthogonal views in FIGS. 6 to 8. It should be appreciated that FIG. 7 is also a plan view of the first embodiment. In order to prevent a repetition, FIGS. 6 to 8 are not described in detail.

A plan view of a retaining splint 12 to be used in connection with the second embodiment of the invention is shown in FIG. 9. The retaining splint 12 is provided with slots 13 so dimensioned that the legs 20, 30 can pass through them. In one side of the retaining splint 12, there are wire guiding notches 14.

Figure 10:
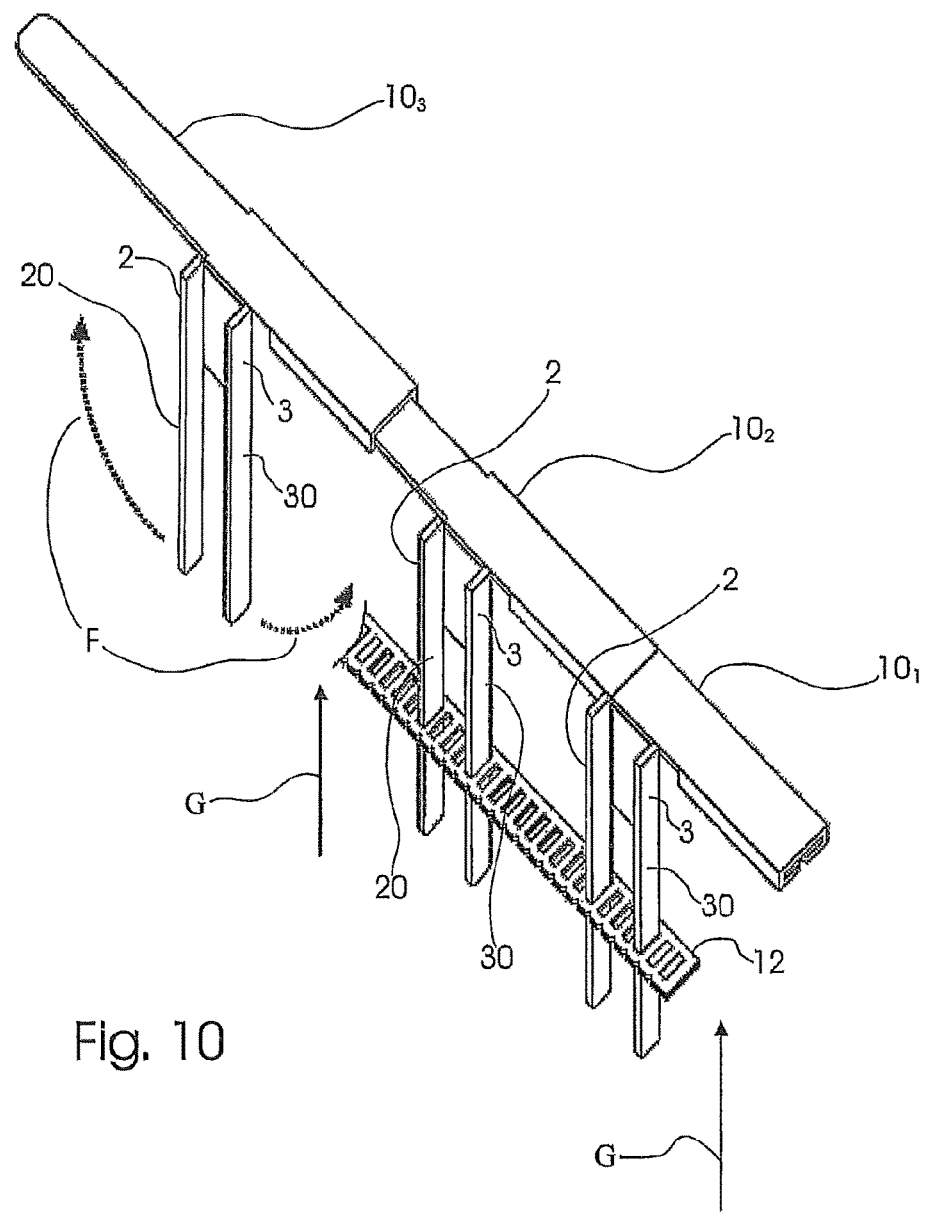
FIG. 10 shows in a perspective view a sternum reinforcing device, in a configuration during use in the method of the invention; the device has three elongated members as that one in FIG. 5, which are mutually consecutively engaged and it is further provided with a retaining splint (partially shown) as that one in FIG. 9.

In the method of the invention, a plurality of elongated modular members $10_1, 10_2, \ldots, 10_n$ are connected together by fitting the male arm 6 of a modular member in the female arm 7 of a consecutive modular member, as already explained for the first embodiment. When a sufficient number of elongated reinforcing members is reached, the installation in the thorax can be performed, by fitting male and female arms also not completely, in case, in order to respect the intercostal spaces. In FIG. 10 there is shown how to fit legs 20, 30 of the retaining splint 12 in the direction of arrows G-G to create an internal greater clamping before rotating the same legs in the direction of arrows F-F.

Figure 11:
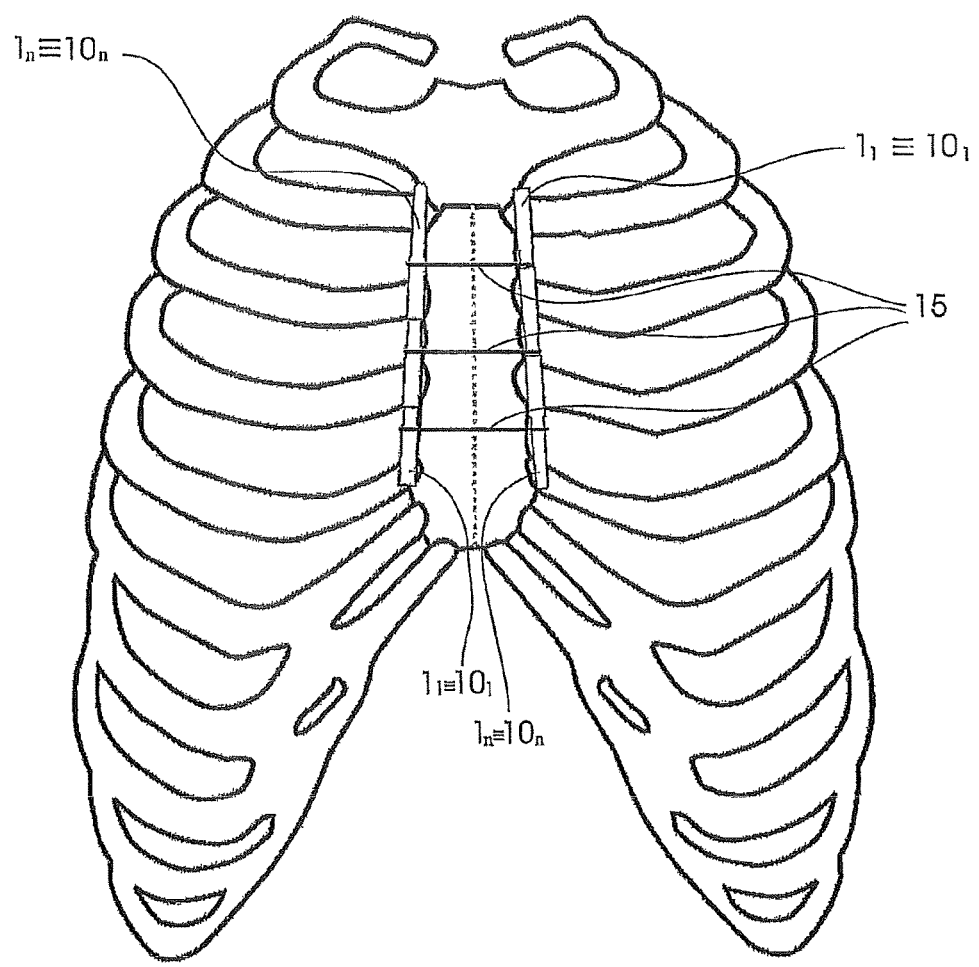
FIG. 11 shows in a diagrammatic perspective view reinforcing devices according to the present invention, which are bilaterally fitted in a sternum according to the method of the invention.

As shown in FIG. 11, two series of elongated reinforcing members are fitted from the front of the thorax, on anterior edge portions of a sternum that was subjected to a sternotomy or partial fracture. FIG. 11 refers to the second embodiment, but it could refer also to the first one. If there are the legs 20, 30, once they are fitted, they are bent as indicated by the arrows F in opposite direction to be anchored in the internal part of the thorax. The legs 20, 30 can be bent after the retaining splint 12 has been fitted, which generates a better distribution of stresses in the thorax. At the end, the two series of reinforcing devices are locked by a wire 15 passing between the edges 2, 3 of each body portion 4. Although not shown in the drawings, the body portion 4 could be suitably bent to create a central guiding surface for the wire 14 already limited by the lateral edges 2, 3 bent outwards.

In such a way, the reinforcing device can be installed only where it is required. The tying wire is surrounded by the reinforcing device, and it will not imply the risk of sternal dehiscence due to loosening of wire or other complications, such as the rubbing of the sternal wires in the normal respiratory movements of the thorax.

By virtue of the particular reinforcing device according to the invention, the sternum can be closed, besides by traditional wires, also by tapes and bands, which are suitably received between the edges 2, 3 of the body portion 4.

The elongated members can be used in a required number, and form together a single reinforcing group. Although in FIG. 11, the elongated members are positioned both on one side and the other of the sternum in order to fully reinforce it, a less number of them can be used to reinforce only or partially a sternal half or both.

The use of the reinforcing devices can be avoided in those cases in which the sternum is in such good conditions that they are not required.

The persons skilled in the field will understand that modifications and variations can be made to the device as above set forth. Although in the embodiments described and illustrated the connection parts forms prismatic couplings, they could create different forms of coupling, either movable or adjustable, between an elongated member and another one. For example, the coupling of at least to two pins, projecting upwards from an elongated member and being movable in a slot of a consecutive member could be chosen. Also the shapes of the parts can be different. For example, the body portion could be arranged not angularly to the remaining elongated member, but with some convexity fitting the lateral configuration of the sternum. It is intended that all modifications, if any, to the device, do not take away the device from the scope of the invention as set forth in the enclosed claims.

What is claimed is:

1. A method for reinforcing a sternum after a sternotomy or a sternal fracture, comprising the step of applying a reinforcing device, said method comprising:
    providing a plurality of elongated members forming a sternum reinforcing group extending on a surface portion along a longitudinal lateral edge of the sternum and fixed to said sternum, wherein the elongated members of the plurality of elongated members are each provided with a first connection part and a second connection part;
    providing said first and second connection parts being in the form of arms, wherein a first one of the arms extends in a first direction with respect to a central portion and a second one of the arms extends in a second direction with respect to said central portion, the second direction being opposite to the first direction;
    joining said first connection part of a first of said plurality of said elongated members with a second connection part of a preceding elongated member of the reinforcing group along the longitudinal lateral edge of the sternum;
    joining said second connection part of said first elongated member with a first connection part of a following elongated member of the reinforcing group along the same longitudinal lateral edge of the sternum;
    fitting a projecting portion provided at each of said plurality of elongated members in an intercostal space adjacent to the longitudinal lateral edge of the sternum.

2. The method according to claim 1, further comprising forming the connection parts of said elongated members as prismatic couplings with the corresponding connection parts of the respective preceding and following elongated member of the group.

3. The method according to claim 1, further comprising making the elongated members from a biocompatible, shaped and bent plate material.

4. The method according to claim 1, further comprising shaping said projecting portion for the intercostal space as a body portion for each of said elongated members extending between said connection parts and at right angles to them.

5. The method according to claim 4, further comprising shaping said body portion to be U-shaped having parallel free edges, orthogonally bent outwards, to enclose between them a clamping element which clamps the elongated member to the sternum.

6. The method according to claim 5, further comprising making said clamping element of a stainless steel wire.

7. The method according to claim 5, further comprising making said free edges of the U-shaped projecting portion extend from the projecting portion in the form of legs and fitting said legs in the intercostal space of the thorax of a patient, laterally to the sternum, and bending said legs in a mutually opposite direction, on the internal side of the thorax.

8. The method according to claim 7, further comprising providing a separated splint provided with a multiplicity of slots for the passage and the retaining of said legs before the legs being bent from the body portion in a mutually opposite direction.

9. The method according to claim 8, further comprising providing said splint, on one side thereof, with guiding notches and accommodating said clamping element in said guiding notches.

10. The method according to claim 1, further comprising providing said first connection part with a male arm and slidingly fitting said male arm in a corresponding second connection part of a preceding elongated member.

11. The method according to claim 10, further comprising providing said male arm with a rectangular flat cross-section profile.

12. The method according to claim 1, further comprising providing said second connection part with a female arm and slidingly fitting said female arm in a corresponding first connection part of the following elongated members.

13. The method according to claim 12, further comprising providing said female arm with a hollow channel-shaped cross-section.

14. The method according to claim 1, further comprising fitting the elongated members of said reinforcing group bilaterally to the sternum along two sternum longitudinal lateral edges.

15. The method according to claim 1, further comprising fixing two series of elongated members to the sternum, each along a respective sternum longitudinal lateral edge.

16. The method according to claim 15, further comprising a locking the two series of elongated members to the sternum by a clamping element passing between edges of the elongated members.

17. The method according to claim 1, further comprising interpenetrating said elongated members.

18. The method according to claim 1, further comprising abutting the end of the first or second connecting part of one member against the projecting portion of an adjacent member.

19. The method according to claim 1, further comprising coupling the first connection part of one elongated member slidably with the second connection part of a preceding or following elongated member of the reinforcing group along the longitudinal lateral edge of the sternum.

20. The method according to claim 19, further comprising adjusting the two elongated members to a rib width of a patient by selecting an amount of mutual sliding between said first and second connection part such that the two elongated members are spaced from each other so that the two elongated members are adjusted to a rib width of a patient.

21. The method according to claim 1, further comprising closing the sternum by tapes and/or bands received between edges of one or more elongated members.

22. A method for reinforcing a sternum after a sternotomy or a sternal fracture, said method comprising:
   applying a plurality of elongated members along at least one longitudinal lateral edge of the sternum, wherein the elongated members are each provided with a first connection part and a second connection part;
   slidably joining a first connection part of a first elongated member with a second connection part of an adjacent preceding elongated member along the longitudinal lateral edge of the sternum;
   slidably joining a second connection part of the first elongated member with a first connection part of an adjacent following elongated member along the same longitudinal lateral edge of the sternum;
   fitting a projecting portion of one or more of said elongated members in an intercostal space adjacent to the longitudinal lateral edge of the sternum; and
   fixing the elongated members to the sternum.

* * * * *